United States Patent [19]
Nilsson

[11] Patent Number: 5,273,034
[45] Date of Patent: Dec. 28, 1993

[54] IMPLANTABLE MEDICAL APPARATUS FOR RATE ADAPTIVE STIMULATION OF A HEART

[75] Inventor: Kenth-Ake-Sune Nilsson, Akersberga, Sweden

[73] Assignee: Siemens Aktiengesellschaft, Munich, Fed. Rep. of Germany

[21] Appl. No.: 872,901

[22] Filed: Apr. 22, 1992

[30] Foreign Application Priority Data

Apr. 26, 1991 [SE] Sweden .................... 9101276

[51] Int. Cl.$^5$ ............................................. A61N 1/00
[52] U.S. Cl. ............................................ 607/18
[58] Field of Search ................ 128/419 PG, 419 D

[56] References Cited

U.S. PATENT DOCUMENTS

| | | |
|---|---|---|
| 4,535,774 | 8/1985 | Olson .................. 128/419 PG |
| 4,702,253 | 10/1987 | Nappholz et al. . |
| 4,884,576 | 12/1989 | Alt . |
| 4,901,725 | 2/1990 | Nappholz et al. . |
| 4,919,136 | 4/1990 | Alt . |
| 5,003,976 | 4/1991 | Alt . |

Primary Examiner—Lee S. Cohen
Assistant Examiner—Marianne Parker
Attorney, Agent, or Firm—Hill, Steadman & Simpson

[57] ABSTRACT

An implantable medical apparatus for stimulating a heart at a variable stimulation rate dependent on the respiratory rate, tidal volume, heart rate and stroke volume includes a measurement apparatus which measures impedance around the heart, a filter unit which splits the impedance signal into high-frequency and a low-frequency signal portions and two analyzers which respectively evaluate the signal portions and which emit the four parameter values as output signals. The product of respiratory rate times tidal volume is formed in a control apparatus. This product corresponds to respiratory minute volume, and the product of heart rate times stroke volume corresponds to cardiac output. Cardiac output is multiplied by a constant, and respiratory minute volume is subtracted from the product thus formed. The resulting different is equal to zero when blood oxygenation is optimum. The control apparatus controls the stimulation rate on the basis of the magnitude and sign of the difference.

8 Claims, 1 Drawing Sheet

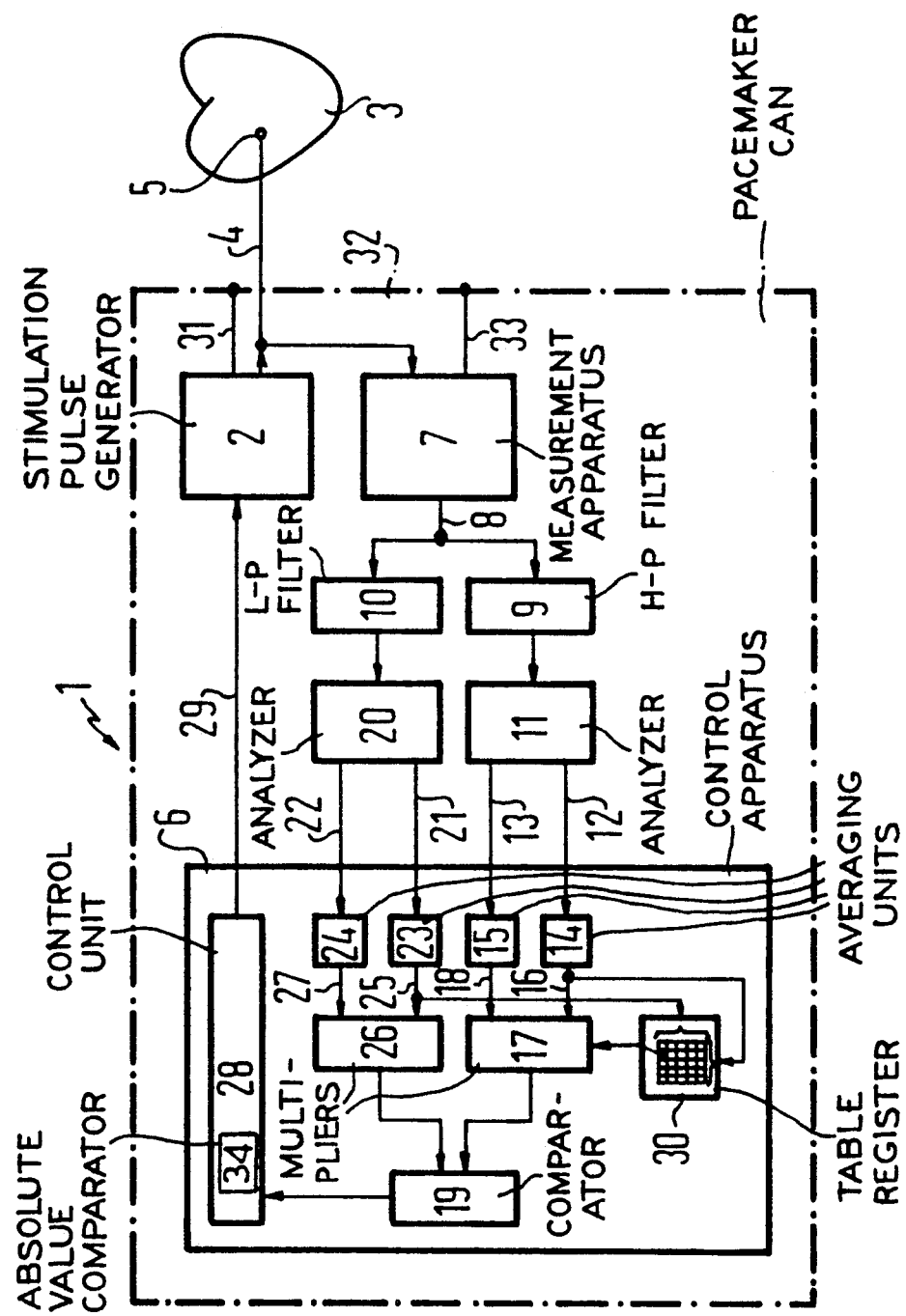

IMPLANTABLE MEDICAL APPARATUS FOR RATE ADAPTIVE STIMULATION OF A HEART

BACKGROUND OF THE INVENTION

1. Field of the Invention

The invention relates to an implantable medical apparatus for stimulating the heart of a patient, which generates a measurement signal dependent upon impedance in the area around the heart from which a heart rate signal, a stroke volume signal, a respiratory rate signal and a tidal volume signal are derived, and wherein the rate at which the stimulation pulse generator provides stimulation pulses is controlled based on these signals.

2. Description of the Prior Art

A pacemaker for stimulation of a heart is disclosed in German OS 37 32 640, corresponding to U.S. Pat. No. 4,884,576, wherein the stimulation is associated with the pacemaker wearer's level of physical activity. The pacemaker has a stimulation pulse generator which generates and delivers stimulation pulses with a waveform and at a rate governed by a control apparatus. The pacemaker also includes an impedance meter, which records the impedance variations arising in the body primarily because of cardiac and pulmonary activity, to sense physical activity. The impedance signal emitted by the impedance meter is split by two signal filters into a low-frequency signal portion corresponding to pulmonary tidal volume and respiratory rate and a high-frequency signal portion corresponding to cardiac stroke volume and heart rate. The respective signal portions are then analyzed in separate signal analyzers connected to the control apparatus.

The stimulation rate of this known pacemaker is determined by the relation between heart rate and respiratory rate, represented by a single characteristic. The control apparatus can then, on the basis of the other parameters, displace the characteristic so the stimulation rate at a given respiratory rate value becomes dependent on the other parameters. For example, the characteristic can be displaced so the stimulation rate increases when stroke volume increases, even if respiratory rate does not change.

The objective of controlling heart rate is to control the blood's oxygenation. Increased physical activity increases the need for oxygen delivery. In a healthy person, this is attained by an increase in pulmonary minute volume, which is a calculated average value for the volume of air inspired per minute, and cardiac output, which is a calculated average measure of the volume of blood ejected by the heart per minute. Pulmonary minute volume is thus the product of respiratory rate times tidal volume, and cardiac output is the product of heart rate times stroke volume.

However, air in the lungs is not replaced as effectively at a fast respiratory rate as at a slow respiratory rate. As a result, a dead-space volume develops in the lungs, thereby reducing oxygen supplies in the lungs and, accordingly, oxygenation of the blood. In a similar manner, a fast heart rate also reduces oxygenation of the blood, since blood then passes through the lungs more rapidly than at a slower heart rate.

SUMMARY OF THE INVENTION

An object of the present invention is to provide an apparatus which controls heart rate in a reliable, uncomplicated manner so oxygenation of the blood is maintained on an essentially constant level.

The invention solves the above problem with a control apparatus in a heart stimulation apparatus of the type described above which contains a first multiplier in which the heart rate signal and stroke volume signal are multiplied by one another, a second multiplier in which the respiratory rate signal and the tidal volume signal are multiplied by one another and a subtractor in which the difference between the output signal from the first multiplier and the output signal from the second multiplier is formed and this difference compared to a preset value, whereupon the control apparatus controls the rate at which the stimulation pulse generator delivers stimulation pulses on the basis of the derivative of the difference from and the preset value.

The invention is based on the realization that the ratio between pulmonary minute volume and cardiac output is essentially constant. This results in substantially constant oxygenation of the blood when the stimulation rate is governed by changes in that ratio. The preset value is established on the basis of each patient's physical circumstances and capability.

Maintenance of oxygenation becomes more effective and reliable because the control apparatus also includes an averaging unit which calculates the average value for each of the heart rate signal, stroke volume signal, respiratory rate signal and tidal volume signal for a preset period of time, and the first multiplier and the second multiplier use the respective average values as input signals. This is because the different parameters, i.e. heart rate, stroke volume, respiratory rate and tidal volume, never change simultaneously or with equal rapidity when the patient's level of activity changes and because short-term changes in parameter values can occur without any change in the level of physical activity.

In an embodiment of the invention, the preset value is one of a plurality of preset values stored in a memory; the values are selected and retrieved from memory on the basis of the prevailing respiratory rate and/or heart rate.

As a result, the apparatus is adaptable on an individual basis to extreme situations, as when the patient holds her/his breath or breathes rapidly. The use of a memory holding a plurality of preset values also results in more accurate and natural stimulation of the patient's heart.

In a further embodiment of the invention, the control apparatus only changes the stimulation pulse rate on the basis of the aforementioned difference between the ratio and the preset value if the absolute value of the difference exceeds a preset threshold value. Since the apparatus does not change the stimulation pulse ratio as long as the absolute value for the difference is less than this preset threshold value, changes which could disturb the patient, such as alternating increases/decreases in the stimulation rate caused by oscillation of the difference around zero, are avoided. As described above for the preset value, it is possible to use a memory with a plurality of threshold values, with the current value, for example being selected on the basis of heart rate and/or respiratory rate.

BRIEF DESCRIPTION OF THE DRAWINGS

The single FIGURE is a schematic block diagram of an apparatus constructed in accordance with the principles of the present invention, in the form of a heart pacemaker.

DESCRIPTION OF THE PREFERRED EMBODIMENT

A pacemaker 1 has a stimulation pulse generator 2 which generates stimulation pulses and delivers then in vivo to a heart 3 via an electrode line 4 having an electrode tip 5. The stimulation pulse generator 2 is connected to the pacemaker can 32 by a first reference connector 31. The stimulation pulse generator 2, is controlled by a control apparatus 6 described below. The pacemaker 1 has a measurement apparatus 7 which is connected to the heart 3 via the electrode line 4 and electrode tip 5 to provide the most effective possible control of the stimulation rate. In the same manner as for the stimulation pulse generator 2, the measurement apparatus 7 is connected to the pacemaker can 32 with a second reference connector 33. The measurement apparatus 7 measures impedance changes in body tissue around the heart 3, changes largely caused by heart rate and the stroke volume of the heart 3 and by respiratory rate and tidal volume.

The output signal from the measurement apparatus 7 is fed through a signal line 8 to a high-pass filter 9 and a low-pass filter 10. The high-pass filter 9 passes only the component of the measurement signal whose frequency is associated with changes in heart rate and stroke volume. The measurement signal portion passed by the high-pass filter 9 is fed to the first analyzer 11 in which the measurement signal portion is analyzed. The first analyzer 11 performs an evaluation of the frequency and amplitude of the input signal and delivers a heart rate signal via a heart rate signal line 12 and a stroke volume signal via stroke volume signal line 13 to the control apparatus 6. In the control apparatus 6, the heart rate signal is fed to a first averaging unit 14 which continuously calculates a current average value for the heart rate during a period preceding the current point in time. In the corresponding manner, an average value for the stroke volume signal is calculated in a second averaging unit 15 in the control apparatus 6.

The averaged heart rate signal is fed through a signal line 16 to a first multiplier 17, and the averaged stroke volume signal is also fed to the first multiplier 17 through a signal line 18. The product of the signals for averaged heart rate and averaged stroke volume is formed in the first multiplier 17, thereby supplying a measure of cardiac output. These signals are simultaneously multiplied by a preset constant K which is obtained as described below. The constant K corresponds to the relation which must prevail between a patient's pulmonary minute value and cardiac output for optimum oxygenation of the blood. The output signal from the first multiplier 17 serves as a first input signal to a subtractor 19.

The measurement signal portion from the low-pass filter 10 is processed in an analogous manner. This filter passes only the component of the measurement signal whose frequency is associated with changes in respiratory rate and tidal volume. The measurement signal portion from the low-pass filter 10 is fed to a second analyzer 20 in which the measurement signal portion is analyzed and split into a respiratory rate signal and a tidal volume signal. The respiratory rate signal is fed through a respiratory rate signal line 21 to a third averaging unit 23 in the control apparatus 6, and the tidal volume signal is fed through a tidal volume line 22 to a fourth averaging unit 24 in the control apparatus 6.

The averaged respiratory rate signal and the average tidal volume signal are respectively fed through a signal line 25 and a signal line 27 to a second multiplier 26. The product of the two signals is formed in the second multiplier 26, and a pulmonary minute volume signal is obtained. This pulmonary minute volume signal is fed to the subtractor 19 in which it is subtracted from the signal from the first multiplier 17, which corresponds to the product of cardiac output and a constant. In this manner, the operation $AK-B$, in which A is cardiac output, K is the constant and B is pulmonary minute volume, is performed. In principle, this difference should be equal to 0, i.e. $B/A = K$ for oxygenation to remain unchanged irrespective of the level of physical activity.

The difference is fed to a control unit 28 in the control apparatus 6 which, on the basis of the magnitude of the difference and its sign (positive or negative), sends an order to the stimulation pulse generator 2 via a control line 29 for an increased in heart rate, a reduction in heart rate or retention of heart rate. Control is exercised here in an interval between a minimum heart rate and a maximum heart rate.

The aforementioned constant K is one of a plurality of constants which apply to different values for heart rate and respiratory rate. Thus, the control apparatus 6 contains a table register 30 to hold the different constants. This register receives the averaged heart rate, via the signal line 16, as an initial input signal and receives, via the signal line 25, the averaged respiratory rate as a second input signal. The two input signals are employed for addressing a table position in the table register 30 which emits the aforementioned constant K as an output signal, corresponding to the addressed table position, to the multiplier 17.

The control unit 28 may contain an absolute value comparator 34 which forms the absolute value of the aforementioned difference and compares this absolute value to a preset threshold, with the control unit 28 changing the stimulation rate only if this absolute value exceeds the threshold value. A register table containing a plurality of selectable threshold values may be provided, useable similar to the table resistor 30.

In the Figure, the function of the control apparatus 6 is shown by the use of different function blocks, but the functions of the different blocks could also be performed by a microprocessor.

Although the present invention has been described with reference to a specific embodiment, those of skill in the art will recognize that changes may be made thereto without departing from the scope and spirit of the invention as set forth in the appended claims.

I claim as my invention:

1. An implantable medical apparatus for in vivo stimulation of a heart in a patient, said apparatus comprising:
   means for generating and delivering stimulation pulses in vivo to a heart at a stimulation pulse rate;
   measurement means for generating a measurement signal dependent upon impedance in an area surrounding said heart, said measurement signal containing a mixture of low-frequency signal components and high-frequency signal components;
   filter means for splitting said measurement signal into a low-frequency signal portion and a high-frequency signal portion;
   first analyzer means for deriving a heart rate signal and a stroke volume signal from said high-frequency signal portion;

second analyzer means for deriving a respiratory rate signal and a tidal volume signal from said low-frequency signal portion;

first multipler means for multiplying said heart rate signal and said stroke volume signal to form a first product;

second multiplier means for multiplying said respiratory rate signal and said tidal volume signal to form a second product;

comparator means for forming a ratio of said first and second products and for comparing said ratio to a preset value and for forming a difference between said ratio and said preset value; and means for controlling said stimulation pulse rate of said means for generating and delivering stimulation pulses on the basis of said difference.

2. An apparatus as claimed in claim 1, wherein said controlling means includes means for forming an average over a preset period of time for each of said heart rate signal, said stroke volume signal, said respiratory signal and said tidal volume signal, and wherein said first multiplier means multiplies said average of said heart rate signal and said average of said stroke volume signal to form said first product and wherein said second multiplier means multiplies said average of said respiratory rate signal and said average of said tidal volume signal for forming said second product.

3. An apparatus as claimed in claim 1, further comprising:

memory means for storing a plurality of preset values; and means for selecting one of said stored preset values from said memory means on the basis of at least one of a current respiratory rate and a current heart rate as said preset value for use in said comparator means.

4. An apparatus as claimed in claim 1, wherein said controlling means includes means for forming the absolute value of said difference and for changing said stimulation rate only if said absolute value exceeds a preset threshold value.

5. A method for operating an implantable medical apparatus for in vivo stimulation of a heart in a patient, said method comprising the steps of:

generating and delivering stimulation pulses in vivo to a heart at a stimulation rate;

generating a measurement signal depending upon impedance in an area surrounding said heart, said measurement signal including low-frequency signal components and high-frequency signal components;

splitting said measurement signal into a low-frequency signal portion and a high-frequency signal portion;

deriving a heart rate signal and a stroke volume signal from said high-frequency signal portion;

deriving a respiratory rate signal and a tidal volume signal from said low-frequency signal portion;

multiplying said heart rate signal and said stroke volume signal to form a first product;

multiplying said respiratory rate signal and said tidal volume signal to form a second product;

forming a ratio of said first and second products and comparing said ratio to a preset value and forming a difference between said ratio and said preset value; and controlling the stimulation rate of said stimulation pulse generator dependent on said difference.

6. A method as claimed in claim 5, comprising the additional step of forming an average value for each of said heart rate signal, said stroke volume signal, said respiratory rate signal and said tidal volume signal over a preset period of time, wherein the step of forming said first product is further defined by multiplying said average value of said heart rate signal and said average value of said stroke volume signal to form said first product, and wherein the step of forming said second product is further defined by multiplying said average value of said respiratory rate signal and said average value of said tidal volume signal to form said second product.

7. A method as claimed in claim 5, comprising the additional steps of:

storing a plurality of preset values in a memory; and selecting one of said preset values, for use as said preset value in said comparing step, on the basis of at least one of a current respiratory rate or current heart rate.

8. A method as claimed in claim 5, comprising the additional steps of:

forming an absolute value of said difference;

comparing said absolute value to a preset threshold; and changing said stimulation rate only if said absolute value exceeds said preset threshold.

* * * * *